(12) United States Patent
Chopp et al.

(10) Patent No.: US 9,149,509 B2
(45) Date of Patent: Oct. 6, 2015

(54) METHODS FOR IMPROVING NEUROLOGICAL OUTCOME AFTER NEURAL INJURY AND NEURODEGENERATIVE DISEASE

(75) Inventors: Michael Chopp, Southfield, MI (US); Zhenggang Zhang, Troy, MI (US); Daniel C. Morris, Grosse Point Park, MI (US)

(73) Assignee: HENRY FORD HEALTH SYSTEM, Detroit, MI (US)

( * ) Notice: Subject to any disclaimer, the term of this patent is extended or adjusted under 35 U.S.C. 154(b) by 0 days.

(21) Appl. No.: 13/258,687

(22) PCT Filed: Mar. 26, 2010

(86) PCT No.: PCT/US2010/028839
§ 371 (c)(1),
(2), (4) Date: Sep. 22, 2011

(87) PCT Pub. No.: WO2010/111598
PCT Pub. Date: Sep. 30, 2010

(65) Prior Publication Data
US 2012/0021992 A1    Jan. 26, 2012

Related U.S. Application Data

(60) Provisional application No. 61/163,556, filed on Mar. 26, 2009.

(51) Int. Cl.
*A61K 38/17* (2006.01)
*A61P 25/32* (2006.01)
*A61K 38/22* (2006.01)

(52) U.S. Cl.
CPC .................................. *A61K 38/2292* (2013.01)

(58) Field of Classification Search
CPC .................................................. A61K 38/2292
See application file for complete search history.

(56) References Cited

U.S. PATENT DOCUMENTS

| | | | |
|---|---|---|---|
| 2007/0111931 A9 | 5/2007 | Kleinman et al. | |
| 2008/0039389 A1 | 2/2008 | Weiss et al. | |
| 2008/0274098 A1 | 11/2008 | Goldstein et al. | |
| 2010/0190713 A1* | 7/2010 | Bevec et al. | 514/12 |

FOREIGN PATENT DOCUMENTS

| | | | |
|---|---|---|---|
| CN | 101102784 A | 1/2008 | |
| JP | 04234325 A | 8/1992 | |
| JP | 2008-526986 A | 7/2008 | |
| WO | 2006/076588 A1 | 7/2006 | |
| WO | 2007/084544 A2 | 7/2007 | |
| WO | 2009033816 A2 | 3/2009 | |

OTHER PUBLICATIONS

't Hart et al., Modelling of multiple sclerosis: lessons learned in a non-human primate, Oct. 2004, The Lancet Neurology 3(10):588-597.*
Wekerle et al., Animal models of multiple sclerosis, 2006, Drug Discovery Today: Disease Models 3(4):359-367.*
Akiyama et al., "Inflammation and Alzheimer's disease", Neurobiology of Aging, 21, (2000) pp. 383-421, Jan. 2000.
Office Action issued in Chinese Patent Application No. 201080013941.9 on Feb. 7, 2013 along with English translation, 12 pages.
Supplementary European Search Report dated Oct. 31, 2012 in EP 10 75 6916, 6 pgs.
H. Yang et al.: "The Promotive Effects of Thymosin β4 on Neuronal Survival and Neurite Outgrowth by Upregulating L1 Expression," Neurochem. Res., 2008, vol. 33, pp. 2269-2280.
Popoli et al., "Neuroprotective Effects of Thymosin B4 in Experimental Models of Excitotoxicity" Annals of the New York Academy of Sciences, 1112, (2007) pp. 219-224.
Van Kesteren et al., "Local Synthesis of Actin-Binding Protein β-Thymosin Rehgulates Neurite Outgrowth" The Journal of Neuroscience, vol. 26, No. 1 (2006) pp. 152-157.
Sun et al., "Neurotrophic Roles of the Beta-Thymosins in the Development and Regeneration of the Nervous System" Annals of the New York Academy of Science, vol. 1112 (2007) pp. 210-218.
Office Action issued in Japanese Patent Appln. No. 2012-502285 on Apr. 15, 2014 along with English translation, 8 pages.

* cited by examiner

*Primary Examiner* — John Ulm
(74) *Attorney, Agent, or Firm* — Rothwell, Figg, Ernst & Manbeck, P.C.

(57) ABSTRACT

Thymosin β4 can be used to treat neuronal and brain injuries that are accompanied by neuronal cell death or injury, including injuries caused by stroke or trauma and injuries caused by neurological and neurodegenerative disease. In particular, stroke and multiple sclerosis are examples of conditions which may be ameliorated by treatment with thymosin β4. Thymosin β4 has been found to restore neurological tissue through several effects on several neurological parameters which are improved by administration of thymosin β4 to a subject in need of neurological tissue restoration. For example, thymosin β4 improves axonal myelination, migration of neural progenitor cells, neural progenitor cell proliferation, differentiation of neural progenitor cells into mature neurons, differentiation of neural progenitor cells into mature glia, nerve regeneration, and brain remodeling at locations of brain injury.

10 Claims, 9 Drawing Sheets

METHODS FOR IMPROVING NEUROLOGICAL OUTCOME AFTER NEURAL INJURY AND NEURODEGENERATIVE DISEASE

This application is a 35 U.S.C. §371 National Phase Entry Application from PCT/US2010/028839, filed Mar. 26, 2010, and designating the United States, which claims the benefit of U.S. provisional patent application Ser. No. 61/163,556, filed Mar. 26, 2009, the contents of which are hereby incorporated by reference in their entirety.

BACKGROUND OF THE INVENTION

1. Field of the Invention

The present invention relates to oligodendrogenesis. In particular, the present invention relates to methods of treatment with thymosin β4.

2. Background of the Art

Stroke is the leading cause of morbidity and disability. Functional neurological recovery from stroke commonly occurs, but is often incomplete. Functional recovery after stroke may be related to remodeling of the injured brain, which includes cerebral angiogenesis and neurogenesis. Neurological impairment also occurs in a variety of other diseases. Sudden occlusion of a cerebral artery induces severe neurological impairment while demyelination of axons from multiple sclerosis causes an insidious and cruel impairment of neurological function. Thus, how to induce axonal plasticity and oligodendrogenesis and to promote functional recovery after neuronal injury are areas of intense interest.

Thymosin β4 is a peptide that has been shown to promote cardiomyocyte migration and survival in ischemic myocardial infarction mice. In addition, thymosin β4 has been shown to regulate vasculogenesis, angiogenesis and arteriogenesis in the post-natal and adult murine cardiac myocardium.

While thymosin β4 has been shown to be effective in wound healing and cardiomyocyte survival, there is no evidence or suggestion that it has any effect on stroke or multiple sclerosis. Therefore, there remains a need for a treatment for stroke and multiple sclerosis, as well as a treatment for neural injury and neurodegenerative disease.

SUMMARY OF THE INVENTION

Embodiments of the present invention provide a method of treating stroke, including the steps of administering thymosin β4, improving functional neurological outcome, and treating stroke.

Further embodiments of the present invention also provide a method of myelinating damaged neurons by administering thymosin β4, promoting migration and differentiation of oligodendrocyte progenitor cells and differentiation of oligodendrocyte progenitor cells into mature oligodendrocytes, and causing oligodendrocytes to myelinate damaged axons.

Additional embodiments of the present invention provide a method of proliferating neural progenitor cells by administering thymosin β4.

Additional embodiments of the present invention provide a method of treating neural injury, including the steps of administering thymosin β4.

Additional embodiments of the present invention also provide a method of treating multiple sclerosis, including the steps of administering thymosin β4, improving functional neurological outcome, and treating multiple sclerosis.

Additional embodiments of the present invention provide a method of treating neurodegenerative disease, including the steps of administering thymosin β4, and treating neurodegenerative disease.

BRIEF DESCRIPTION OF THE DRAWINGS

Other advantages of the present invention will be readily appreciated as the same becomes better understood by reference to the following detailed description when considered in connection with the accompanying drawings.

DETAILED DESCRIPTION OF THE PREFERRED EMBODIMENTS

Embodiments of the present invention include methods of improving functional neurological outcome after the onset of neurological diseases, such as stroke and multiple sclerosis, by the administration of thymosin β4.

Thymosin is an actin-binding protein. β-thymosins are a subgroup of thymosin that are the primary regulators of unpolymerized actin. β-thymosins maintain the small cytoplasmic pool of free G-actin monomers required for rapid filament elongation and allow the flux of monomers between the thymosin-bound pool and F-actin. Thymosin β4 is the most common form of β-thymosin, and it sequesters G-actin, preventing polymerization.

More specifically, thymosin β4 is administered to a patient suffering from a stroke after the stroke has occurred in order to treat stroke. The thymosin β4 can be administered right after stroke has occurred. Alternatively, administration can be performed 24 hours or later after the stroke has occurred. The thymosin β4 provides restorative effects well after damage to the brain has occurred. Thymosin β4 increases oligodendrocyte progenitor cell proliferation and differentiation, which subsequently myelinates injured axons. This improves neurological function after stroke.

More specifically, thymosin β4 shifts oligodendrocyte progenitor cells to more mature oligodendrocyte phenotypes. In other words, thymosin β4 promotes oligodendrocyte progenitor cell migration followed by differentiation to mature oligodendrocytes at the site of neural injury. These mature oligodendrocytes produce myelin, which insulates axons and improves nerve impulse transmission. Thus, the mature oligodendrocytes function as promoters of nerve regeneration and/or remodeling in the brain and other places where nerve damage has occurred. In addition, there also may be a separate role for oligodendrocyte progenitor cells in promoting recovery, independent of their differentiation into mature oligodendrocytes and subsequent myelination of axons.

Therefore, embodiments of the present invention also include a method of myelinating damaged axons by administering thymosin β4, promoting migration and proliferation of oligodendrocyte progenitor cells and differentiation of oligodendrocyte progenitor cells into mature oligodendrocytes, and causing oligodendrocytes to myelinate damaged axons.

Figure 8:
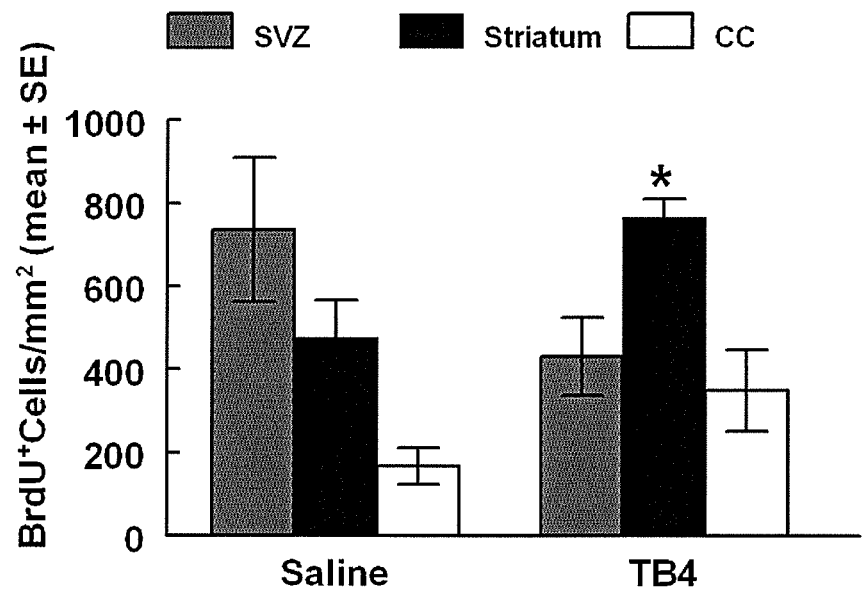
FIG. 8 is a bar graph providing data of amounts of BrdU+ cells (a marker of dividing cells) for control and test groups in an embolic stroke model.

Embodiments of the present invention also include a method of proliferating neural progenitor cells by administering thymosin β4. Neural progenitor cells generate various types of neural cells, such as, but not limited to, neurons and glia. Example 1 and FIG. 8 show that new neural progenitor cells were detected with BrdU staining after administration of thymosin β4. Treatment of embolic stroke rats with thymosin β4 demonstrated a relative 42% increase in BrdU expression in the striatum or myelinated region of the rat brain. The increase in BrdU expression reflects DNA synthesis and cellular proliferation. Increased cellular proliferation in the brain is not a characteristic finding in the normal adult brain. This finding, together with a significant increase in CNP (11%), a marker of mature oligodendrocytes, and NG-2 (47%), a marker of immature oligodendrocytes, is unique in that there appears to be a shift of neural progenitor cells to oligoprogenitor cells and mature oligodendrocytes. It is this remyelination process that contributes the significant neurological functional recovery that is observed in the thymosin beta-4 treatment rats. In other words, by stimulating the neural progenitor cells with thymosin β4, more mature types of neural cells can be produced that can replace damaged neural cells, thereby effectively treating diseased conditions where damaged neural cells are present.

Embodiments of the present invention also include a method of treatment of neural injury, by administering the thymosin β4 to a patient suffering from the neural injury. Any neural injury can be treated, such as traumatic brain injury (TBI). The thymosin β4 functions in the manner described above to repair the injured or damaged neurons.

The thymosin β4 also can be administered to a patient suffering from multiple sclerosis. Administration to the patient can occur at any stage of the disease. In multiple sclerosis, the immune system attacks the central nervous system and demyelinates neurons. Through the proliferation and differentiation of oligodendrocytes and myelination of injured axons, thymosin β4 essentially reverses the effects of multiple sclerosis, allowing patients to regain nerve communication. Therefore, embodiments of the present invention provides a method of treating multiple sclerosis.

Thymosin β4 is also administered to treat neurodegenerative diseases in general, not limited to multiple sclerosis, in embodiments of the invention. Neurodegenerative diseases are caused by degeneration of neurons as a whole or degeneration of the myelin sheath. Examples include, but are not limited to, alcoholism, Alexander's disease, Alper's disease, Alzheimer's disease, Amyotrophic lateral sclerosis, Ataxia telangiectasia, Batten disease, bovine spongiform encephalopathy, Canavan disease, Cockayne syndrome, corticobasal degeneration, Creutzfeld-Jakob disease, frontotemporal lobar degeneration, Huntington's disease, HIV-associated dementia, Kennedy's disease, Krabbe's disease, Lewy body dementia, neuroborreliosis, Machado-Joseph disease, narcolepsy, Niemann Pick disease, Parkinson's disease, Pelizaeus-Merzbacher disease, Pick's disease, primary lateral sclerosis, prion diseases, progressive supranuclear palsy, Refsum's disease, Sandhoff's disease, Schilder's disease, subacute combined degeneration of spinal cord, spinocerebellar ataxia, spinal muscular atrophy, Steele-Richardson-Olszewski disease, and Tabes dorsalis.

There are several advantages to the present invention. The methods herein are useful for treatment of many different forms of neural injury and neurodegenerative disease, including stroke and multiple sclerosis. The mechanism of thymosin β4's action is related to adult neural progenitor cell proliferation and differentiation to oligodendrocytes and subsequent myelination of injured axons. Furthermore, thymosin β4 can be used to treat stroke 24 hours or more after onset, significantly increasing the number of available patients eligible for treatment as compared to methods in the prior art.

It is also unexpected that thymosin β4 is able to treat stroke, neural injury, and neurodegenerative disease after it has occurred. Thymosin β4 acts as a neurorestorative agent when administered 24 hours or less after onset of stroke by a mechanism of axonal remodeling. It is demonstrated herein that improvement in function and oligodendrogenesis occurs by the unique mechanism of migration and differentiation of oligodendrocytes.

The animal models used in the example below are standard models for stroke and multiple sclerosis. Data obtained from the animal experiments are directly applicable to humans. Therefore, administration of the thymosin β4 improves the neurological outcome of humans.

The compound of the present invention is administered and dosed in accordance with good medical practice, taking into account the clinical condition of the individual patient, the site and method of administration, scheduling of administration, patient age, sex, body weight and other factors known to medical practitioners. The pharmaceutically "effective amount" for purposes herein is thus determined by such considerations as are known in the art. The amount must be effective to achieve improvement including but not limited to improved survival rate or more rapid recovery, or improvement or elimination of symptoms and other indicators as are selected as appropriate measures by those skilled in the art.

In embodiments of methods according to the present invention, the compound of the present invention can be administered in various ways. It should be noted that it can be administered as the compound and can be administered alone or as an active ingredient in combination with pharmaceutically acceptable carriers, diluents, adjuvants and vehicles. The compounds can be administered orally, subcutaneously or parenterally including intravenous, intraarterial, intramuscular, intraperitoneally, intratonsillar, and intranasal administration as well as intrathecal and infusion techniques. Implants of the compounds are also useful. The patient being treated is a warm-blooded animal and, in particular, mammals, including man. The pharmaceutically acceptable carriers, diluents, adjuvants and vehicles as well as implant carriers generally refer to inert, non-toxic solid or liquid fillers, diluents or encapsulating material not reacting with the active ingredients of the invention.

The doses can be single doses or multiple doses over a period of several days. The treatment generally has a length proportional to the length of the disease process and drug effectiveness and the patient species being treated.

When administering the compound of the present invention parenterally, it will generally be formulated in a unit dosage injectable form (solution, suspension, emulsion). The pharmaceutical formulations suitable for injection include sterile aqueous solutions or dispersions and sterile powders for reconstitution into sterile injectable solutions or dispersions. The carrier can be a solvent or dispersing medium containing, for example, water, ethanol, polyol (for example, glycerol, propylene glycol, liquid polyethylene glycol, and the like), suitable mixtures thereof, and vegetable oils.

Proper fluidity can be maintained, for example, by the use of a coating such as lecithin, by the maintenance of the required particle size in the case of dispersion and by the use of surfactants. Nonaqueous vehicles such a cottonseed oil, sesame oil, olive oil, soybean oil, corn oil, sunflower oil, or peanut oil and esters, such as isopropyl myristate, may also be used as solvent systems for compound compositions. Additionally, various additives which enhance the stability, sterility, and isotonicity of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. In many cases, it will be desirable to include isotonic agents, for example, sugars, sodium chloride, and the like. Prolonged absorption of the injectable pharmaceutical form can be brought about by the use of agents delaying absorption, for example, aluminum monostearate and gelatin. According to the present invention, however, any vehicle, diluent, or additive used would have to be compatible with the compounds.

Sterile injectable solutions can be prepared by incorporating the compounds utilized in practicing the present invention in the required amount of the appropriate solvent with various of the other ingredients, as desired.

A pharmacological formulation of the present invention can be administered to the patient in an injectable formulation containing any compatible carrier, such as various vehicle, adjuvants, additives, and diluents; or the compounds utilized in the present invention can be administered parenterally to the patient in the form of slow-release subcutaneous implants or targeted delivery systems such as monoclonal antibodies, vectored delivery, iontophoretic, polymer matrices, liposomes, and microspheres. Examples of delivery systems useful in the present invention include those described in, for example, U.S. Pat. Nos. 5,225,182; 5,169,383; 5,167,616; 4,959,217; 4,925,678; 4,487,603; 4,486,194; 4,447,233; 4,447,224; 4,439,196; and 4,475,196, the disclosures of which are hereby incorporated by reference. Many other such implants, delivery systems, and modules are well known to those skilled in the art.

The invention is further described in detail by reference to the following experimental examples. These examples are provided for the purpose of illustration only, and are not intended to be limiting unless otherwise specified. Thus, the present invention should in no way be construed as being limited to the following examples, but rather be construed to encompass any and all variations which become evident as a result of the teaching provided herein.

EXAMPLES

Methods

Effectiveness of treatment with thymosin β4 was tested in stroke (middle cerebral artery occlusion (MCAo)) rats and in experimental autoimmune encephalomyelitis (EAE) mice (a well-established in vivo model for multiple sclerosis). Both the stroke rats and the EAE mice were treated with 6 mg/kg thymosin β4 intraperitoneally (IP) in a volume of 0.3 mL twenty-four hours after stroke or after the day of immunization in the EAE model and then every three days (6 mg/kg IP) for four additional doses. An equal volume of saline was administered (IP) to a group of both stroke rats and EAE mice as a control. Bromodeoxyuridine (BrdU; 100 mg/kg) was administered (IP) daily for seven days, initiated 24 hours after MCAo to label proliferating cells. Behavioral tests (adhesive removable test and NSS (Neurological Severity Score)) were performed immediately before treatment and at days 1, 7, 14, 21, 28, 35, 42, 49, and 56 days after MCAo and up to 30 days in the EAE mouse model. All rats were sacrificed 56 days after MCAo; EAE mice were sacrificed at 30 days.

Results

Figure 1:
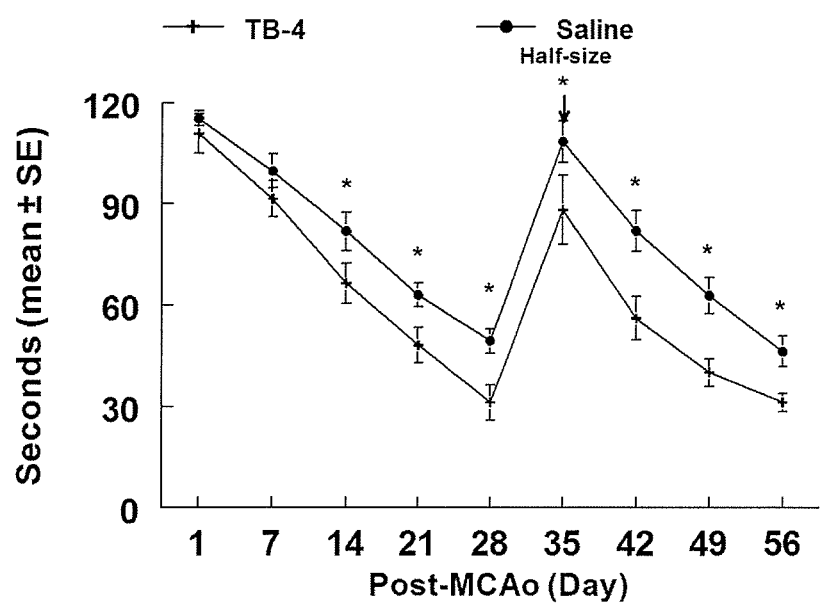
FIG. 1 is a graph of adhesive removal test (a behavioral test) results after embolic right middle cerebral artery occlusion (MCAo). Overall treatment effect ($p<0.01$; $n=18$). Individual time point effect (*$p<0.05$).
Figure 2:
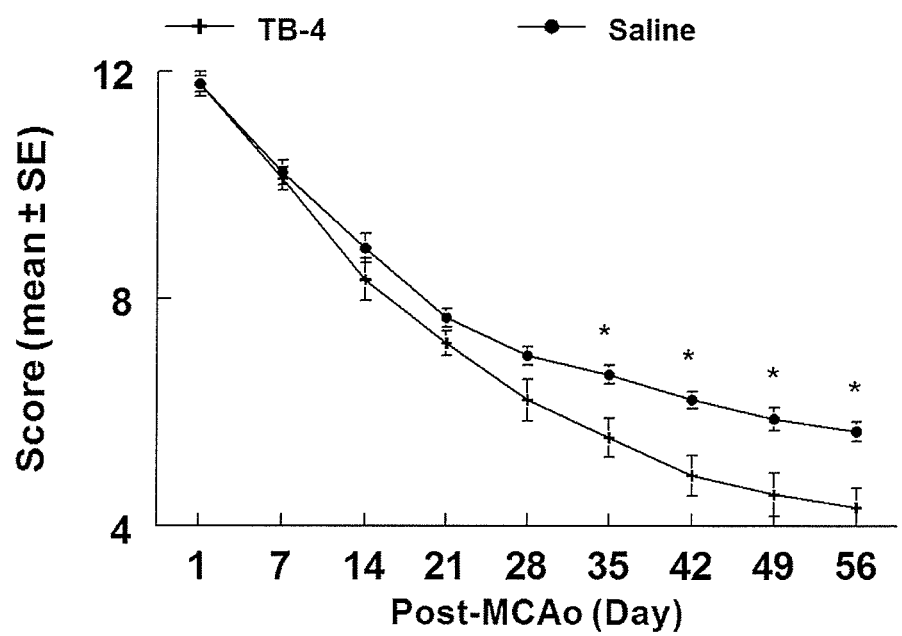
FIG. 2 is a graph showing data for neurological severity score (NSS) after MCAo. Overall treatment effect ($p<0.01$; $n=18$). Individual time point effect (*$p<0.05$).
Figure 3:
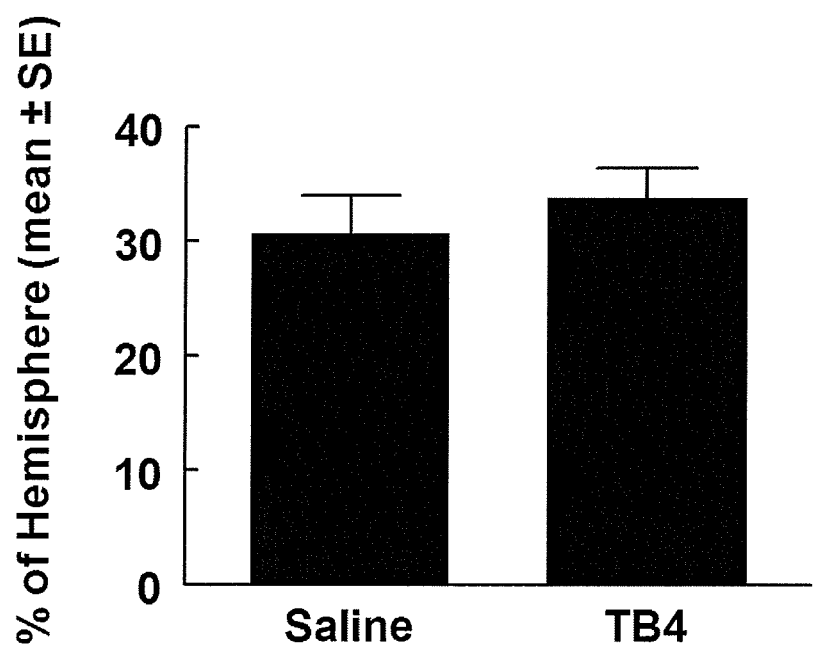
FIG. 3 is a bar graph showing lesion volume in control and test groups in an embolic stroke model. $n=18$; $p<0.05$.
Figure 4:
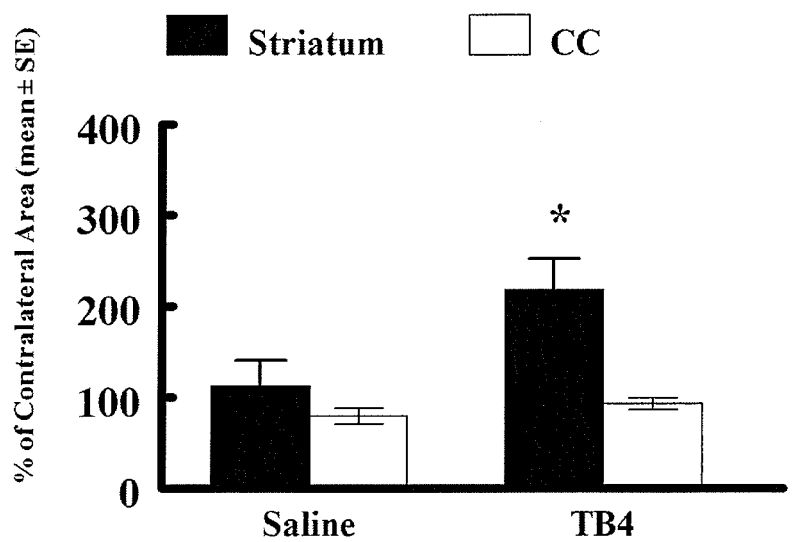
FIG. 4 is a bar graph showing numbers of myelinated axons in control and test groups by Bielschowsky and Luxol Fast Blue staining in an embolic stroke model ($n=18$; *$p<0.05$)
Figure 5:
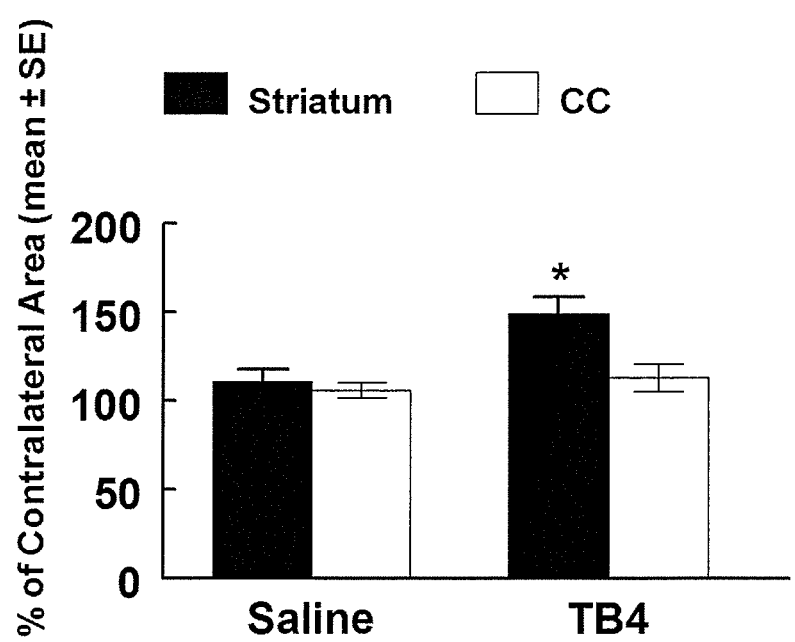
FIG. 5 is a bar graph providing data for CNPase (a marker of mature oligodendrocytes) in control and test groups in an embolic stroke model ($n=18$; *$p<0.05$)
Figure 6:
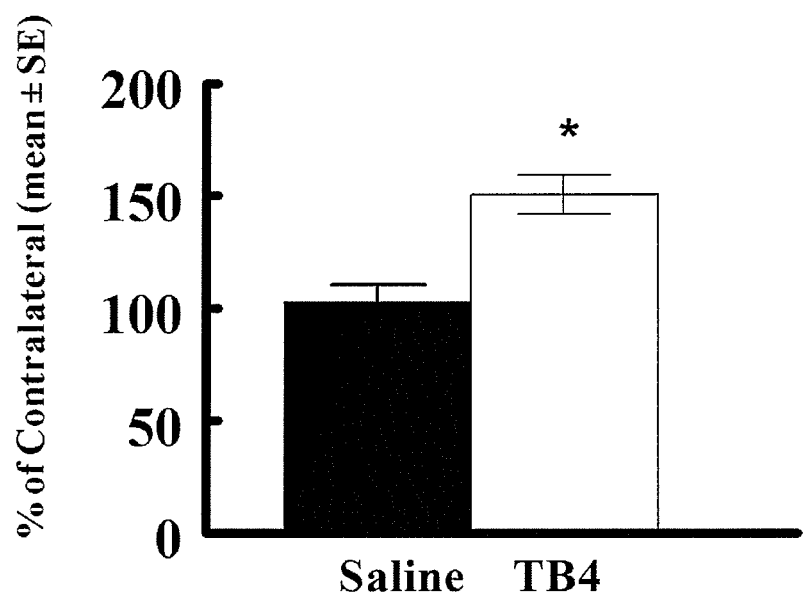
FIG. 6 is a bar graph providing data of amounts of NF-H (a marker of axons) for control and test groups in an embolic stroke model ($n=18$; *$p<0.05$).
Figure 7:
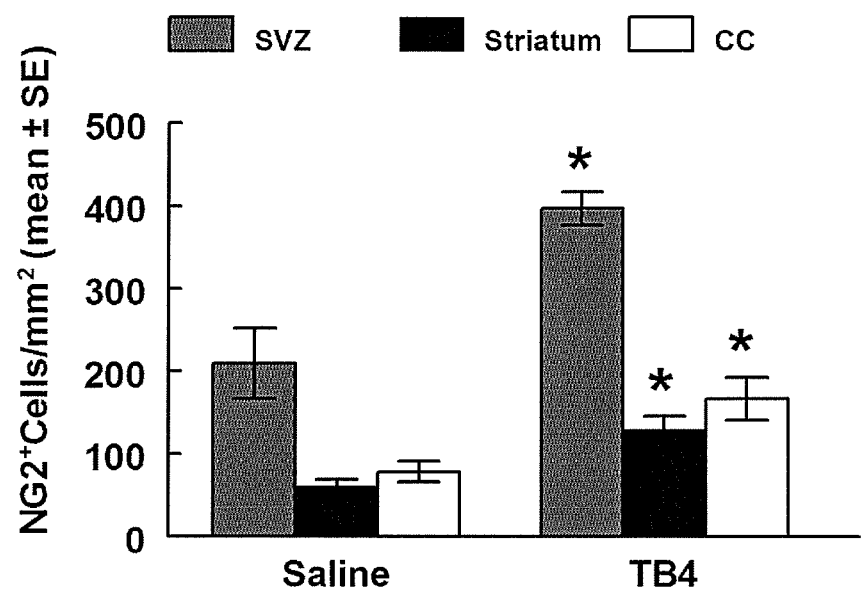
FIG. 7 is a bar graph providing data of amounts of NG-2+ cells (a marker of oligodendrocyte progenitor cells) for control and test groups in an embolic stroke model ($n=18$; *$p<0.05$).

Significant functional improvement, measured by an array of behavioral tests beginning at 21 days after stroke onset, was observed (FIG. 1-2, $p<0.05$). Infarct lesion volumes of the embolic stroke model were similar in both control and treated groups (FIG. 3, $p<0.05$). The number of myelinated axons (FIG. 4, $p<0.05$) and the number of oligodendrocyte progenitors and matured oligodendrocytes (FIGS. 5-7, $p<0.05$) were increased in the thymosin β4-treated group after MCAo. Moreover, cellular proliferation was also increased in this model after thymosin β4 treatment as evidenced by increased BrdU expression and increased number of BrdU immunoreactive cells (FIG. 8, $p<0.05$).

Figure 9:
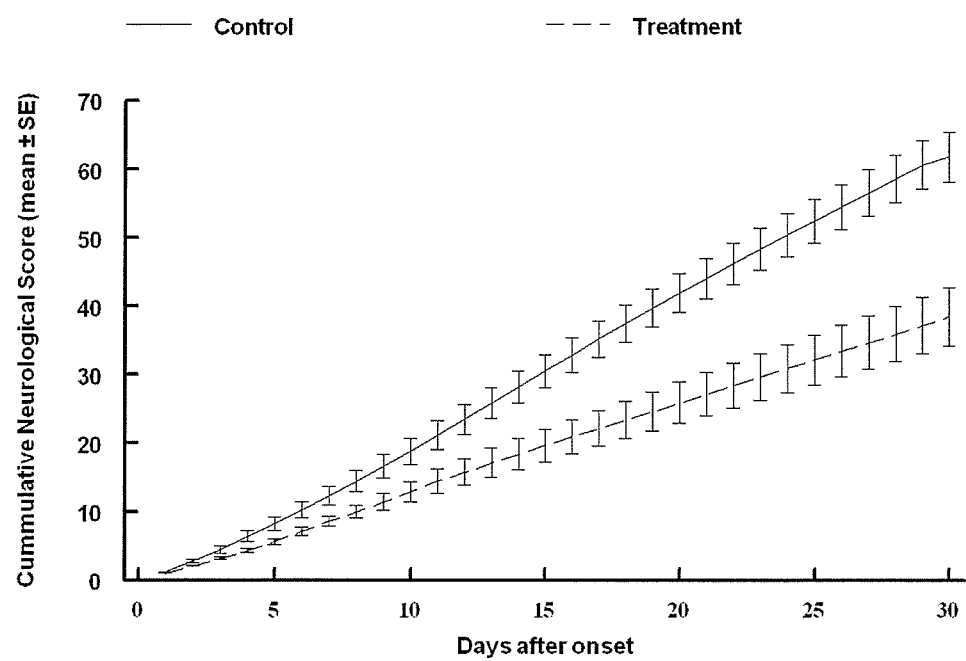
FIG. 9 is a graph of the functional neurological score for control and test mouse groups after EAE (experimental autoimmune encephalomyelitis) ($n=21$). Relative neurology score recovery, $p<0.01$.

Results from the EAE mouse model demonstrated a robust improvement in functional neurological score for thymosin β4-treated mice compared to control. See FIG. 9 ($p<0.01$).

CONCLUSIONS

Treatment with thymosin β4 improved functional neurological outcome in both a rat model of embolic stroke and a mouse multiple sclerosis model. Mechanisms of improvement are due to increased oligodendrocyte progenitor cell proliferation and differentiation and subsequent myelination of injured axons. These results predict results expected in humans, showing that thymosin β4 can be used to treat stroke and multiple sclerosis, among other neurological diseases.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that the invention may be practiced otherwise than as specifically described.

The invention claimed is:

1. A method of treating neural injury by myelinating damaged neurons, which comprises administering to a subject in need thereof a pharmaceutically effective amount of thymosin β4, so as to myelinate said damaged neurons.

2. The method of claim 1 wherein injured axons are myelinated.

3. The method of claim 1 wherein said thymosin β4 is administered as a single dose.

4. The method of claim 1 wherein said thymosin β4 is administered as multiple doses.

5. The method of claim 1 wherein said thymosin β4 is administered in injectable form.

6. A method of treating neural injury by myelinating damaged neurons, which comprises administering to a subject in need thereof a pharmaceutically effective amount of thymosin β4, so as to myelinate said damaged neurons, wherein said neural injury is due to a demyelinating disease.

7. The method of claim 6 wherein injured axons are myelinated.

8. The method of claim 6 wherein said thymosin β4 is administered as a single dose.

9. The method of claim 6 wherein said thymosin β4 is administered as multiple doses.

10. The method of claim 6 wherein said thymosin β4 is administered in injectable form.

* * * * *